United States Patent [19]

Leslie et al.

[11] Patent Number: 4,997,977
[45] Date of Patent: Mar. 5, 1991

[54] PROCESS FOR THE PRODUCTION OF ESTERS EXHIBITING NONLINEAR OPTICAL RESPONSE

[75] Inventors: Thomas M. Leslie, Lebanon; Bernice I. Feuer, Berkeley Heights; Mark J. Sebastian, Plainfield, all of N.J.

[73] Assignee: Hoechst Celanese Corp., Somerville, N.J.

[21] Appl. No.: 405,490

[22] Filed: Sep. 11, 1989

[51] Int. Cl.$^5$ .............................................. C07C 69/52
[52] U.S. Cl. .................... 560/221; 526/312; 560/55; 560/85; 560/103; 560/121; 560/123; 560/124; 560/182; 560/205; 560/231
[58] Field of Search ............... 260/397.5; 526/312; 560/221

[56] References Cited

U.S. PATENT DOCUMENTS

| | | | |
|---|---|---|---|
| 4,540,743 | 9/1985 | Schulz et al. | 522/95 |
| 4,808,332 | 2/1989 | Demartino et al. | 526/312 |
| 4,810,338 | 3/1989 | DeMartino et al. | 204/157.88 |

Primary Examiner—Paul J. Killos
Assistant Examiner—Steven B. Jervey
Attorney, Agent, or Firm—Michael W. Ferrell

[57] ABSTRACT

This invention provides multistep process embodiments for the production of novel esters which exhibit nonlinear optical response.

A process embodiment is illustrated by the reaction of a Schiff base with a substituted acetic acid to form a stilbene alcohol intermediate:

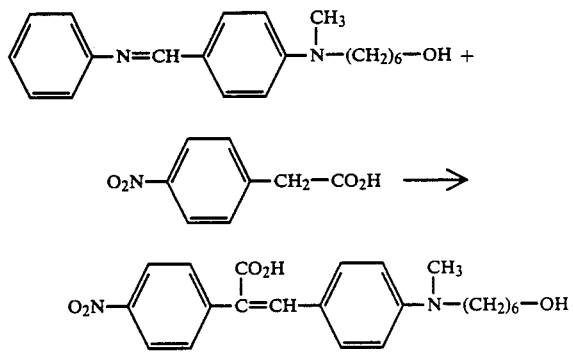

The stilbene alcohol intermediate is decarboxylated, and then is esterified in the presence of a pyridine type catalyst to provide an ester with a conjugated structure.

36 Claims, No Drawings

PROCESS FOR THE PRODUCTION OF ESTERS EXHIBITING NONLINEAR OPTICAL RESPONSE

CROSS-REFERENCE TO RELATED PATENT APPLICATIONS

The present patent application has subject matter related to the disclosures of patent application Ser. No. 405,503, filed Sept. 11, 1989; and 405,804, filed Sept. 11, 1989.

BACKGROUND OF THE INVENTION

Polymers with a comb structure of pendant side chains are a new class of organic materials which exhibit interesting optical properties.

In U.S. Pat. Nos. 4,694,066; 4,755,574; and 4,762,912 liquid crystalline polymers are described which have pendant side chains which exhibit nonlinear optical susceptibility, in addition to mesogenic properties.

U.S. Pat. No. 4,792,208 discloses nonlinear optically responsive organic compounds and side chain polymers in which the molecular dipoles have an electron donor moiety linked through a conjugated $\pi$ bonding system to an electron acceptor sulfonyl moiety.

U.S. Pat. Nos. 4,808,332 and 4,810,338 disclose polymers with pendant side chains in which a stilbene-type structure or a diphenylbutadiene-type structure is in conjugation with an electron-donating group and an electron-withdrawing group. These extended conjugated dipolar electronic systems exhibit an exceptionally high level of second order nonlinear optical susceptibility $\beta$.

Thin films of organic or polymeric materials with large second order nonlinearities in combination with silicon-based electronic circuitry have potential as systems for laser modulation and deflection, information control in optical circuitry, and the like.

Of specific interest with respect to the present invention are publications such as U.S. Pat. Nos. 3,678,082 and 4,540,743 which describe the esterification of alcohols in the presence of an aminopyridine catalyst.

Because of the important applications of nonlinear optically responsive organic compounds and polymerizable monomers, there is increasing research effort to develop new and improved methods for synthesizing the conjugated dipolar electronic structures which provide the desirable optical properties.

Accordingly, it is an object of this invention to provide a novel method for the synthesis of organic compounds and polymerizable monomers which exhibit a high level of nonlinear optical response.

It is a further object of this invention to provide an improved multistep process for the production of acrylate monomers having a chemical structure characterized by an electron-donating group which is linked through a conjugated electronic system to an electron-withdrawing group.

Other objects and advantages of the present invention shall become apparent from the accompanying description and examples.

DESCRIPTION OF THE INVENTION

One or more objects of the present invention are accomplished by the provision of a process for the preparation of an ester which comprises (1) forming a carboxylate intermediate having the formula:

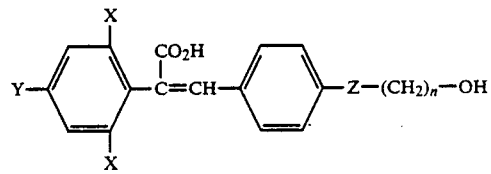

by reacting the following compounds in an organic solvent medium:

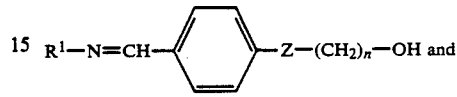

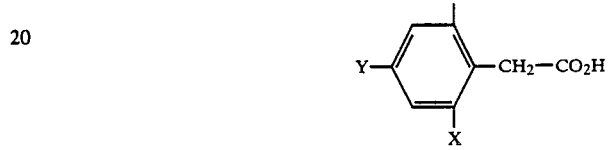

where X is hydrogen or an electron-withdrawing substituent; Y is an electron-withdrawing substituent; Z is —NR—, —S— or —O—; n is an integer with a value of 1-6; R is hydrogen or a $C_1$-$C_4$ alkyl substituent; and $R^1$ is an aliphatic, alicyclic or aromatic radical containing beween about 1-12 carbon atoms; (2) heating the carboxylate intermediate of step (1) in an organic solvent medium under acidic conditions at a temperature between about 40°–150° C. to form a stilbene alcohol intermediate having the formula:

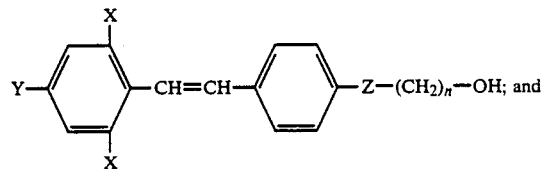

(3) forming an ester having the formula:

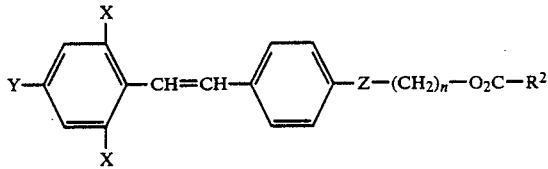

by reacting the stilbene alcohol of step(2) with an anhydride having the formula:

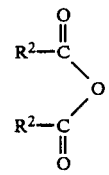

in an organic solvent medium in contact with a catalyst having the formula:

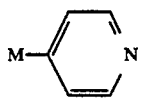

where X, Y, Z and n are as previously defined; $R^2$ is an aliphatic, alicyclic or aromatic substituent containing between about 1-9 carbon atoms; and M is hydrogen or a tertiary amine substituent containing between about 2-6 carbon atoms.

In another embodiment this invention provides a process for the preparation of an ester which comprises (1) forming a carboxylate intermediate having the formula:

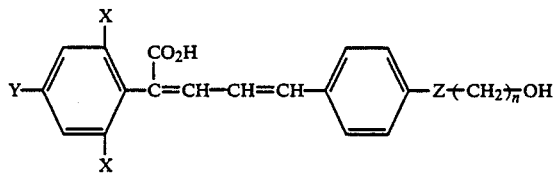

by reacting the following compounds in an organic solvent medium:

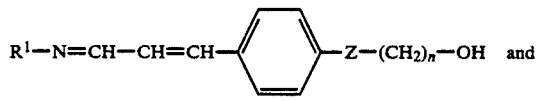

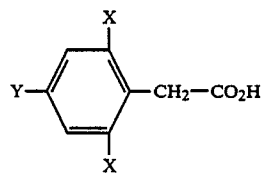

where X is hydrogen or an electron-withdrawing substituent; Y is an electron-withdrawing substituent; Z is —NR—, —S— or —O—; n is an integer with a value of 1-6; R is hydrogen or a $C_1$-$C_4$ alkyl substituent; and $R^1$ is an aliphatic, alicyclic or aromatic radical containing between about 1-12 carbon atoms; (2) heating the carboxylate intermediate of step(1) in an organic solvent medium under acidic conditions at a temperature between 40°-150° C. to form a diphenylbutadiene alcohol intermediate having the formula:

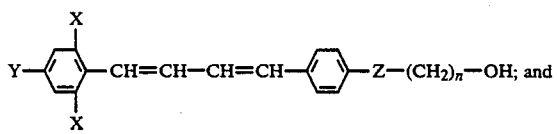

(3) forming an ester having the formula:

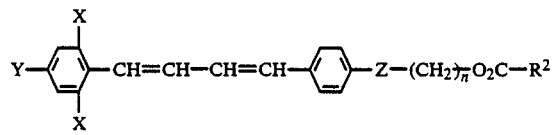

by reacting the diphenylbutadiene alcohol of step (2) with an anhydride having the formula:

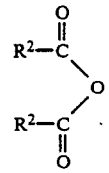

in an organic medium in contact with a catalyst having the formula:

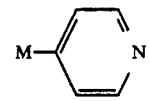

where X, Y, Z and n are as previously defined; $R^2$ is an aliphatic, alicyclic or aromatic substituent containing between about 1-8 carbon atoms; and M is hydrogen or a tertiary amine substituent containing between about 2-6 carbon atoms.

In the above represented process embodiments, the X and Y substituents in the organic structures are illustrated by electron-withdrawing groups which include nitro, cyano, trifluoromethyl acyl, carboxy, alkanoyloxy, aroyloxy, carboxamido, alkoxysulfonyl, aryloxysulfonyl, tricyanovinyl, triflate, and the like.

The $R^1$ substituent in the organic structures is illustrated by aliphatic, alicyclic and aromatic radicals which include methyl, propyl, alkyl, methoxyethyl, 3-hexenyl, octyl, decyl, cyclopentyl, cyclohexyl, phenyl, 4-fluorophenyl, 4-methoxyphenyl, tolyl, 4-pyridyl, and the like.

The $R^2$ substituent in the organic structures is illustrated by aliphatic, alicyclic and aromatic radicals which include methyl, propyl, 3-methoxypropyl, hexyl, heptyl, vinyl 2-propenyl, phenyl, 4-methoxyphenyl, 4-ethoxycarbonylphenyl, and the like.

The step(1) reaction to form the carboxylate intermediate is conducted at a temperature between about 15°-110° C. for a period of about 0.5-24 hours as necessary for completion of the reaction. The step(1) reaction is conducted in an organic medium of one or more solvents such as hexane, benzene, toluene, nitrobenzene, dibutyl ether, dioxane, tetrahydrofuran, dimethylformamide, carbon disulfide, dimethylsulfoxide, acetone, acetonitrile, pyridine, carbon tetrachloride, and the like.

The step(2) reaction to form the stilbene alcohol or diphenylbutadiene alcohol is conducted for a period of about 0.2-24 hours as necessary to complete the reaction.

The step(2) reaction medium is an organic solvent medium of the type described above for step(1). The acidic conditions in step(2) preferably are provided by an organic acid such as formic acid, acetic acid, methacrylic acid, trifluoroacetic acid, benzenesulfonic acid, benzoic acid, and the like.

The step(3) esterification reaction is conducted at a temperature between about 20°-120° C. for a period of about 0.5-24 hours as necessary to complete the reaction. The step(3) reaction medium is an organic solvent medium of the type described above for step(1). A preferred solvent medium for step(3) is an organic tertiary amine such as pyridine, either alone or in admixture with another organic solvent.

An important aspect of the step(3) esterification reaction is the presence of a pyridine or 4-tertiaryamine substituted pyridine catalyst. Illustrative of tertiaryamine substituted pyridine catalysts are 4-dimethylaminopyridine, 4-(1-pyrrolidino)pyridine, 4-(1-piperidino)pyridine, 4-(1-hexahydroazepino)pyridine, 4-(4-morpholino)pyridine, 4-(4-methyl-1-piperidinyl)-pyridine, and the like.

Preparation Of Schiff Base Starting Material

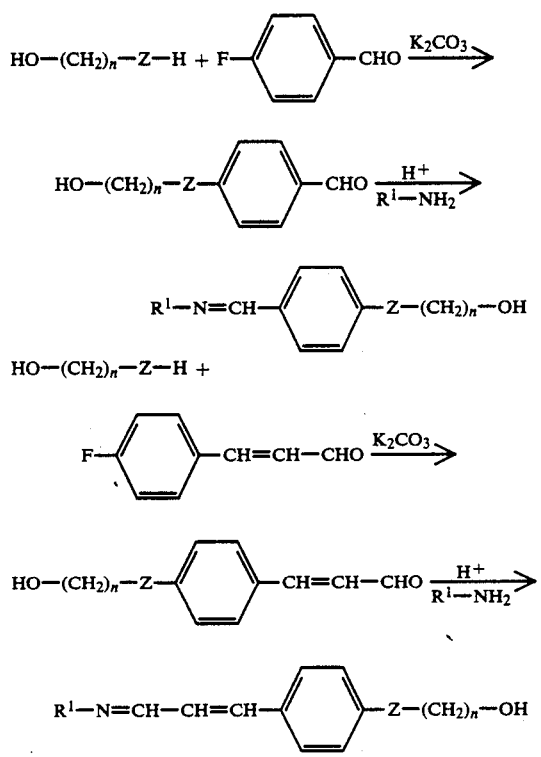

The other reactants utilized in the invention process embodiments are commercially available or can be prepared by synthesis procedures described in the chemical literature. For example, 2,4,6-trinitrophenylacetic acid can be prepared by the reaction of 1-chloro-2,4,6-trinitrobenzene and ethyl malonate in the presence of metallic sodium.

The following examples are further illustrative of the present invention. The components and specific ingredients are presented as being typical, and various modifications can be derived in view of the foregoing disclosure within the scope of the invention.

EXAMPLE I

This Example illustrates the preparation of 4-[N-methacroyloxyethyl)-N-methylamino]-4'-nitrostilbene monomer.

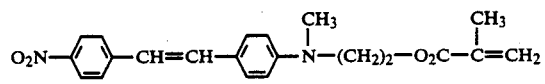

A. Aminobenzaldehyde Starting Material

Following the procedure described in U.S. Pat. No. 4,808,332, a reactor is charged with 2-(methylamino)ethanol (134 g, 1.8 moles), 4-fluorobenzaldehyde (74.4 g, 0.6 mole), potassium carbonate (82.8 g, 0.6 mole) and dimethylsulfoxide (750 ml), and the mixture is heated at 95° C. for 72 hours. The product mixture is cooled and poured into three liters of ice water. The yellow solid that precipitates is filtered, washed with water, and dried in a vacuum oven, mp 72° C. The 4-[N-(2-hydroxyethyl)-N-methylamino]benzaldehyde product is recrystallized from water as needle-like crystals.

B. Schiff Base

4-[N-(2-hydroxyethyl)-N-methylamino]benzaldehyde (179 g, 1.0 mole) and toluene (1.2 liters) are charged to a reaction flask, and the reactor is purged with argon. The reaction medium is heated to reflux under argon, and water is removed with a Dean-Stark trap.

Methanesulfonic acid (0.2 ml) is added to the refluxing solution, and then aniline (102 g, 1.1 moles) is added dropwise, and the heating is continued until about 18 ml of water is removed.

A yellow precipitate forms on cooling, and is separated by filtration and dried, mp 111.9° C.

C. Stilbene Alcohol

A reactor is charged with 4-nitrophenylacetic acid (163 g; 0.9 mole) and two liters of toluene. The mixture is heated at reflux, and water is removed with a Dean-Stark trap.

Schiff base (190 g; 0.75 mole) as prepared above and methacrylic acid (128 ml; 1.5 moles) are added to the reactor contents, and the mixture is heated at 110° C. for two hours. The reaction mixture is cooled to room temperature, and the precipitated product (172 g) is separated by filtration.

The crude product (100 g) is recrystallized from 1.5 liters of acetonitrile to yield magenta crystals, mp 185°–187° C.

D. Acrylate Monomer

A reactor is charged with stilbene alcohol (29.8 g; 0.1 mole) as prepared above, pyridine (300 ml) and dimethylaminopyridine catalyst (2.44 g; 0.02 mole). The reactor contents are heated to 75° C., and methacrylic anhydride (40.1 g; 0.26 mole) is added, and the reaction is conducted at 75° C. for 20 hours.

The product mixture is cooled, and poured into a liter of water. The resultant crystalline precipitate is recovered by filtration, and washed with water and with ether.

The crude product is recrystallized from ethyl acetate to yield orange crystals, mp 152° C.

The corresponding 4-fluoro and 4-trifluoromethyl acrylates are prepared by substituting 4-fluorophenylacetic acid and 4-trifluoromethylphenylacetic acid, respectively, for the 4-nitrophenylacetic acid reactant in the stilbene alcohol preparation described above.

EXAMPLE II

This Example illustrates the preparation of 4-[N-(2-methacroyloxyethyl)-N-methylamino]-2',4'-dinitrostilbene monomer.

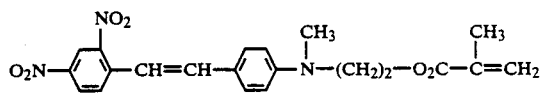

A. Stilbene Alcohol

A reactor is charged with 2,4-dinitrophenylacetic acid (45.23 g, 0.2 mole; Aldrich), toluene (360 ml), and Schiff base (50.9 g, 0.2 mole) as prepared in Example I. The reaction mixture is stirred at room temperature for one hour, then methacrylic acid (34.4 g, 0.4 mole) is added dropwise, and the reactor contents are heated at 75° C. for three hours and at 110° C. for two hours.

On cooling, the product separates as crystals, mp 186°–189° C.

B Acrylate Monomer

A reactor is charged with stilbene alcohol (24 g, 0.07 mole) as prepared above, pyridine (240 ml) and dimethylaminopyridine catalyst (1.71 g, 0.014 mole). The reactor contents are heated to 75° C., and methacrylic anhydride (29 ml, 0.195 mole) is added, and the reaction is conducted at 75° C. for 20 hours.

The product mixture is cooled, and poured into 750 ml of water. The resultant black crystalline precipitate is recovered by filtration and dried at 50° C. in a vacuum oven, mp 122°–125° C. The chemical structure of the product is consistent with a NMR spectral analysis. Recrystallization of the product from ethyl acetate/ethanol (3.2/1) yields shiny black crystals, mp 125°–126° C.

The corresponding oxy-substituted and thio-substituted acrylates are prepared by using ethylene glycol and 2-mercaptoethanol, respectively, in place of the 2-(methylamino)ethanol reactant in the Schiff base preparation described in Example I.

EXAMPLE III

This Example illustrates the preparation of 4-[N-(4-methacroyloxybutyl)-N-ethylamino]-2′,4′,6′-trinitrostilbene.

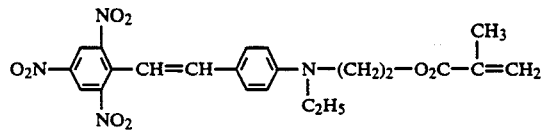

A. Aminobenzaldehyde Starting Material

Following the procedure of Example I, 2-(ethylamino)ethanol is reacted with 4-fluorobenzaldehyde to provide 4-[N-ethyl-N-(2-hydroxyethyl)amino]-benzaldehyde starting material.

B. Schiff Base

Following the procedure of Example I, aminobenzaldehyde starting material as prepared above is reacted with aniline to form a corresponding Schiff base intermediate product.

C. Stilbene Alcohol 2,4,6-Trinitrophenylacetic acid (mp 159°–160° C.) is prepared from 1-chloro-2,4,6-trinitrobenzene and ethyl malonate in the presence of metallio sodium in accordance with a procedure by M. Kimura in J. Pharm. Soc. Jpn., 73, 1216 (1953).

Following the procedure of Example I, a Schiff base as prepared above is reacted with 2,4,6-trinitrophenylacetic acid to provide a corresponding stilbene alcohol product.

D. Acrylate Monomer

Following the procedure of Example I, stilbene alcohol as prepared above is esterified with methacrylic anhydride to provide a corresponding acrylate monomer product.

The corresponding acetate and benzoate esters are prepared by substituting acetic anhydride and benzoic anhydride, respectively, for the methacrylic anhydride reactant in the esterification procedure.

EXAMPLE IV

This Example illustrates the preparation of 4-[N-2-(methacroyloxyethyl)-N-ethylamino]-4′-nitro-1,3-butadiene monomer.

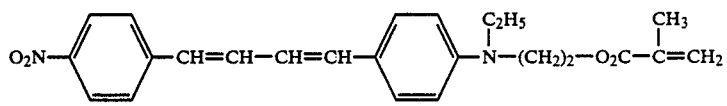

A. Diphenylbutadiene Alcohol

A reactor fitted with a mechanical stirrer, thermometer, Dean Stark trap with a condenser, and an argon bubbler is charged with 360 ml of toluene. The solvent is heated to reflux to remove any water and then cooled to room temperature. To the toluene is added 4-(N-2-hydroxyetyyl-N-ethylamino)cinnamaldehyde, (43.86 g, 0.2 mole) with methanesulfonic acid (0.2 mole %, 0.19 g). The reaction mixture is heated to reflux, and aniline (0.2 mole, 18.6 g) is added dropwise with azeotropic removal of water (3.6 ml) for 18 hours. After cooling to room temperature, 4-nitrophenylacetic acid (43.48 g, 1.238 mole) is added followed by a dropwise addition of methacrylic acid (34.4 g, 0.4 mole). The reaction mixture is stirred at room temperature for 12 hours, heated to 75° C. for 3 hours and then refluxed at 110° C. for 2 hours. The reaction mixture is cooled to room temperature, and the solid diphenylbutadiene alcohol precipitates from solution. The crude product is recovered by filtration, and recrystallized from ethanol.

B. Acrylate Monomer

A reactor fitted with a mechanical stirrer, thermometer and temperature controller is charged with 4-(N-2-hydroxyethyl-N-ethylamino)-4′-nitro-1,4-diphenyl-1,3-butadiene (33.85 g, 0.1 mole), dry pyridine (250 ml) and 4-N,N-dimethylaminopyridine (1.71 g, 0.014 mole). The reaction mixture is heated to 75° C. before beginning the dropwise addition of freshly distilled methacrylic anhydride (29 ml, 0.195 mole). The reaction is maintained at 75° C. for twenty hours, cooled to room temperature, and poured into 750 ml of distilled water. The solid product separates as a precipitate. The precipitate is isolated by filtration, and then dried at 50° C. in a vacuum oven. The crude product is purified by recrystallization from ethanol.

What is claimed is:

1. A process for the preparation of an ester which comprises (1) forming a carboxylate intermediate having the formula:

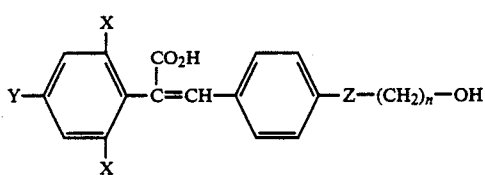

by reacting the following compounds in an organic solvent medium:

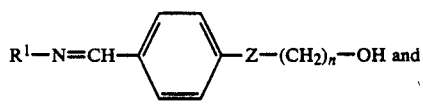

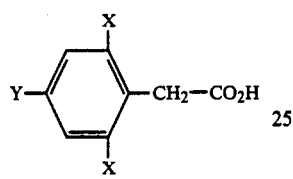

where X is hydrogen or an electron-withdrawing substituent; Y is an electron-withdrawing substituent; Z is —NR—, —S— or —O—, n is an integer with a value of 1-6; R is hydrogen or a $C_1$-$C_4$ alkyl substituent; and $R^1$ is an aliphatic, alicyclic or aromatic radical containing 1-12 carbon atoms; (2) heating the carboxylate intermediate of step (1) in an organic solvent medium under acidic conditions at a temperature of 40° C.-150° C. to form a stilbene alcohol intermediate having the formula:

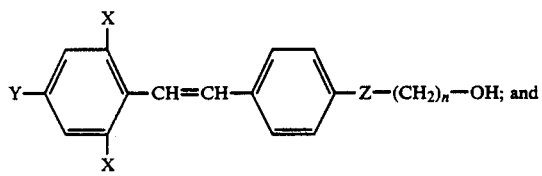

(3) forming an ester having the formula:

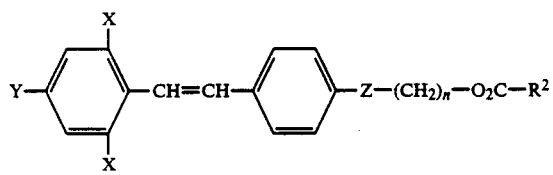

by reacting the stilbene alcohol of step (2) with an anhydride having the formula:

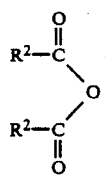

in an organic solvent medium in contact with a catalyst having the formula:

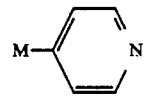

where X, Y, Z and n are as previously defined; $R^2$ is an aliphatic, alicyclic or aromatic substituent containing 1-9 carbon atoms; and M is hydrogen or a tertiary amine substituent containing 2-6 carbon atoms.

2. A process in accordance with claim 1 wherein Y is a nitro substituent.

3. A process in accordance with claim 1 wherein at least one of X is a nitro substituent.

4. A process in accordance with claim 1 wherein Z is —NH— or —NCH$_3$—.

5. A process in accordance with claim 1 wherein $R^2$ is —CH=CH$_2$ or

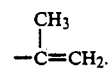

6. A process in accordance with claim 1 wherein the organic solvent medium in step(1) is a hydrocarbon solvent.

7. A process in accordance with claim 1 wherein the step(1) reaction is conducted at a temperature of 15° C.-110° C. for a period of 0.5-24 hours.

8. A process in accordance with claim 1 wherein the organic solvent medium in step(2) is a hydrocarbon solvent.

9. A process in accordance with claim 1 wherein the acidic conditions in step(2) are provided by an organic acid, and the reaction is conducted for a period of 0.2-24 hours.

10. A process in accordance with claim 1 wherein the organic solvent medium in step(3) is a hydrocarbon solvent.

11. A process in accordance with claim 1 wherein the organic solvent medium in step(3) is an organic tertiary amine either alone or in admixture with another organic solvent.

12. A process in accordance with claim 1 wherein the step(3) reaction is conducted at a temperature of 20° C.-120° C. for a period of 0.5-24 hours.

13. A process in accordance with claim 1 wherein the catalyst in step(3) is 4-dimethylaminopyridine.

14. A process in accordance with claim 1 wherein the catalyst in step(3) is 4-(1-pyrrolidino)pyridine.

15. A process in accordance with claim 1 wherein the catalyst in step(3) is 4-(1-piperidino)pyridine.

16. A process in accordance with claim 1 wherein the catalyst in step(3) is 4-(1-hexahydroazepino)pyridine.

17. A process in accordance with claim 1 wherein the catalyst in step(3) is 4-(4-morpholino)pyridine.

18. A process in accordance with claim 1 wherein the catalyst in step(3) is 4-(4-methyl-1-piperidinyl)pyridine.

19. A process for the preparation of an ester which comprises (1) forming a carboxylate intermediate having the formula:

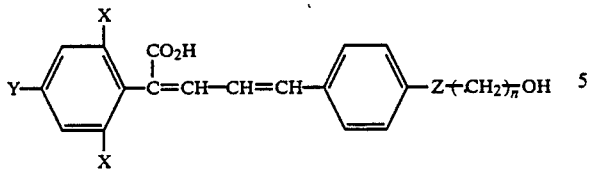

by reacting the following compounds in an organic solvent medium:

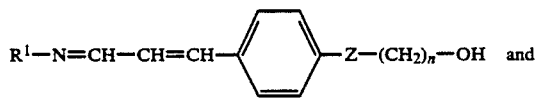

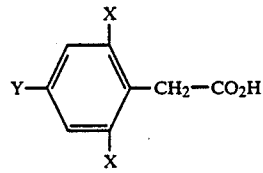

where X is hydrogen or an electron-withdrawing substituent; Y is an electron-withdrawing substituent; Z is —NR—, —S— or —O—; n is an integer with a value of 1–6; R is hydrogen or a $C_1$–$C_4$ alkyl substituent; and $R^1$ is an aliphatic, alicyclic or aromatic radical containing 1–12 carbon atoms; (2) heating the carboxylate intermediate of step(1) in an organic solvent medium under acidic conditions at a temperature between 40° C.–150° C. to form a diphenylbutadiene alcohol intermediate having the formula:

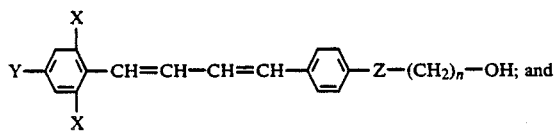

(3) forming an ester having the formula:

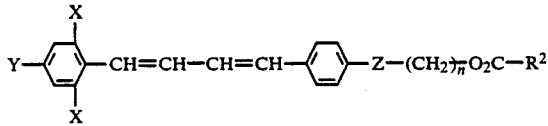

by reacting he diphenylbutadiene alcohol of step(2) with an anhydride having the formula:

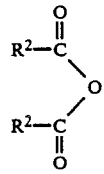

in an organic medium in contact with a catalyst having the formula:

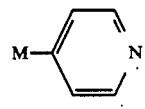

where X, Y, Z and n are as previously defined; $R^2$ is an aliphatic, alicyclic or aromatic substituent containing 1–9 carbon atoms; and M is hydrogen or a tertiary amine substituent containing 2–6 carbon atoms.

20. A process in accordance with claim 19 wherein Y is a nitro substituent.

21. A process in accordance with claim 19 wherein at least one of X is a nitro substituent.

22. A process in accordance with claim 19 wherein Z is —NH— or —NCH$_3$—.

23. A process in accordance with claim 19 wherein $R^2$ is —CH=CH$_2$ or

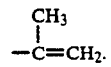

24. A process in accordance with claim 19 wherein the organic solvent medium in step (1) is a hydrocarbon solvent.

25. A process in accordance with claim 19 wherein the step(1) reaction is conducted at a temperature of 15° C.–110° C. for a period of 0.5–24 hours.

26. A process in accordance with claim 19 wherein the organic solvent medium in step(2) is a hydrocarbon solvent.

27. A process in accordance with claim 19 wherein the acidic conditions in step(2) are provided by an organic acid, and the reaction is conducted for a period of 0.2–24 hours.

28. A process in accordance with claim 19 wherein the organic solvent medium in step(3) is a hydrocarbon solvent.

29. A process in accordance with claim 19 wherein the organic solvent medium in step(3) is an organic tertiary amine either alone or in admixture with another organic solvent.

30. A process in accordance with claim 19 wherein the step(3) reaction is conducted at a temperature of 20° C.–120° C. for a period of 0.5–24 hours.

31. A process in accordance with claim 19 wherein the catalyst in step(3) is 4-dimethylaminopyridine.

32. A process in accordance with claim 19 wherein the catalyst in step(3) is 4-(1-pyrrolidino)pyridine.

33. A process in accordance with claim 19 wherein the catalyst in step(3) is 4-(1-piperidino)pyridine.

34. A process in accordance with claim 19 wherein the catalyst in step(3) is 4-(1-hexahydroazepino)pyridine.

35. A process in accordance with claim 19 wherein the catalyst in step(3) is 4-(4-morpholino)pyridine.

36. A process in accordance with claim 19 wherein the catalyst in step(3) is 4-(4-methyl-1-piperidinyl)pyridine.

* * * * *